United States Patent
Depraetere et al.

(10) Patent No.: US 11,591,414 B2
(45) Date of Patent: Feb. 28, 2023

(54) METHOD FOR SEPARATING LARVAE IN A PULP AND A LIQUID FRACTION

(71) Applicants: Circular Organics N.V., Turnhout (BE); VITO NV, Mol (BE)

(72) Inventors: Stefaan Depraetere, Turnhout (BE); Els D'Hondt, Mol (BE); Maarten Uyttebroek, Mol (BE); Bert Van Den Bosch, Mol (BE); Johan Jacobs, Turnhout (BE)

(73) Assignees: CIRCULAR ORGANICS N.V., Turnhout (BE); VITO NV, Mol (BE)

( * ) Notice: Subject to any disclaimer, the term of this patent is extended or adjusted under 35 U.S.C. 154(b) by 400 days.

(21) Appl. No.: 16/759,278

(22) PCT Filed: Oct. 25, 2018

(86) PCT No.: PCT/EP2018/025273
§ 371 (c)(1),
(2) Date: Apr. 24, 2020

(87) PCT Pub. No.: WO2019/081067
PCT Pub. Date: May 2, 2019

(65) Prior Publication Data
US 2021/0221921 A1 Jul. 22, 2021

(30) Foreign Application Priority Data
Oct. 26, 2017 (BE) .................................. 2017/0150

(51) Int. Cl.
| | | |
|---|---|---|
| C08B 37/00 | (2006.01) | |
| C07K 1/14 | (2006.01) | |
| C11B 1/06 | (2006.01) | |
| C07K 14/435 | (2006.01) | |
| C08B 37/08 | (2006.01) | |

(52) U.S. Cl.
CPC ............ C08B 37/0003 (2013.01); C07K 1/14 (2013.01); C11B 1/06 (2013.01); C07K 14/43563 (2013.01); C08B 37/003 (2013.01)

(58) Field of Classification Search
None
See application file for complete search history.

(56) References Cited

U.S. PATENT DOCUMENTS

2018/0016357 A1  1/2018  Berezina et al.

FOREIGN PATENT DOCUMENTS

| EP | 2455445 A1 | 5/2012 |
|---|---|---|
| RU | 2010150667 | 4/2013 |
| WO | WO 2015173449 | 11/2015 |
| WO | WO 2016108033 | 7/2016 |
| WO | WO 2016197057 | 12/2016 |

OTHER PUBLICATIONS

Azagoh C. et al., "Extraction and physicochemical characterization of Tenebrio molitor proteins," Food Research International, 88: 24-31 (2016).
Database WPI Thomson Scientific, London, GB; vol. 2013, No. 66, AN 2013-N290260 XP002786980.
Nwe N. et al., "Chitin and Chitosan from Terrestrial Organisms: Chitin, Chitosan, Oligosaccharides and Their Derivatives: Biological Activities and Applications," CRC Press, pp. 3-10 (2010).
International Preliminary Report on Patentability, dated Apr. 28, 2020, from International Application No. PCT/EP2018/025273, filed on Oct. 25, 2018. 10 pages.
International Search Report and Written Opinion of the International Searching Authority, dated Dec. 14, 2018, from International Application No. PCT/EP2018/025273, filed on Oct. 25, 2018. 14 pages.
Wang J. et al., "Housefly larvae hydrolysate: orthogonal optimization of hydrolysis, antioxidant activity, amino acid composition and functional properties," BMC Research Notes, 6(1):1-10 (2013).

*Primary Examiner* — Layla D Berry
(74) *Attorney, Agent, or Firm* — HoustonHogle LLP

(57) ABSTRACT

The present invention relates to a method for separating larvae into a pulp fraction and a liquid fraction, including the steps of introducing living larvae into a grinding apparatus whist adding water, grinding the larvae by means of counter-rotating screws and separating the ground biomass of larvae into a pulp and liquid fraction. In particular, the invention is applicable to the larvae of the black soldier fly and produces a chitin-rich pulp and a fat-and-protein-rich liquid fraction.

15 Claims, 4 Drawing Sheets

METHOD FOR SEPARATING LARVAE IN A PULP AND A LIQUID FRACTION

RELATED APPLICATIONS

This application is a § 371 National Phase Application of International Application No. PCT/EP2018/025273, filed on Oct. 25, 2018, now International Publication No. WO 2019/081067 A1, published on May 2, 2019, which International Application claims priority to Belgian Application No. BE2017/0150, filed on Oct. 26, 2017, both of which are incorporated herein by reference in their entirety.

FIELD OF THE INVENTION

The present invention relates to a method for separating larvae in a pulp fraction on the one hand and a liquid fraction on the other hand. More specifically, the invention relates to a method whereby the biomass of larvae is separated into a chitin-rich pulp and a fat-and-protein-rich liquid fraction. These fractions can subsequently undergo one or multiple re-application(s) of the method according to the invention, for the purpose of obtaining a more purified chitin-rich pulp fraction on the one hand and a larger fat-and-protein-rich liquid fraction on the other hand.

BACKGROUND OF THE INVENTION

It is well known that, to date, no or insufficient solutions have been made available for processing large quantities of organic waste.

One of the possibilities is to offer organic waste as feed to the larvae of insects, more specifically to the larvae of the black soldier fly (*Hermetia illucens*).

These larvae can process a large amount of organic waste in a relatively short time.

In order to economically optimize the process, the larvae can a.o. be used as a source for fat, proteins and chitin. Methods have been developed to extract those ingredients from the larvae biomass.

Chitin is of particular interest because it finds many applications in the cosmetic and/or medicinal sector, as well as in the processing industry (e.g. in water purification applications) and as an ingredient for animal feed.

However, an economically optimized method of extracting the biomass from such larvae and separating it into the various ingredients is not available at present. Moreover, currently available methods are usually energy-intensive and require high inputs of raw materials, since the presently available practices often lead to a loss of mainly the protein component of the processed biomass.

WO 2016/108033A1, discloses a method for the isolation of one or more desired products from insects, including insects in the adult, larval or nymph stage. More in particular an enzymatic hydrolysis is applied to a fraction obtained from a method comprising grinding of the insects by means of an Angel® juicer apparatus. The method according to WO 2016/108033A1, comprises a step of killing the insects prior to subjecting them to pressing and/or grinding. Thereto, the insects, prior to being fed to the grinding apparatus, are subjected to scalding in water at a temperature of between 95-105° C., in a ratio of the volume of water in ml to the weight of insect in g comprised between 0.3 and 10. As a result, dead insects or larvae are subjected to the grinding operation by the counter-rotating screws of the Angel® juicer. The method disclosed in WO 2016/108033A1 presents the disadvantage that proteins are denatured by the scalding procedure which gives rise to the formation of large protein clusters that are retained within the chitin pulp fraction in the grinding and separation step. The pulp fraction additionally contains a lipid fraction. In order to separate this large portion of proteins from the remainder of the treated insect exoskeletons, an additional and cumbersome process step needs to be implemented, namely an enzymatic hydrolysis of the protein fraction resulting from the application of this method. Such additional process step entails an additional operational cost and a substantial additional investment in machinery; both are required for installing and running the equipment; on top hereof, additional raw materials are required for the execution of such chemical hydrolysis step. As a result, the overall operation becomes economically less attractive. There is therefore a need for a method which permits to separate the biomass of insect larvae more selectively, in particular the larvae of the black soldier fly, into various organic ingredients, particularly in fats, proteins and chitin.

SUMMARY OF THE INVENTION

The aim of the present invention is to solve the aforementioned and other disadvantages by providing a method in which the biomass of larvae can be separated in an economically feasible manner into its constituting ingredients, especially fats, proteins and chitin.

To this end, the invention comprises a method for separating the biomass of larvae into a pulp and a liquid fraction, comprising the following steps:
  a) introducing living larvae into a grinding apparatus whilst adding water;
  b) grinding the larvae by means of the grinding apparatus comprising at least two counter-rotating screws to generate ground biomass and
  c) separating the ground biomass into a pulp and a liquid fraction by means of a transport screw placed in a gradually narrowing cylinder, whereby the cylinder at least over the length of the transport screw is equipped with a mesh-shaped material and pressing, resp. transporting the pulp fraction towards an outlet of the transport screw.

The method of this invention permits to achieve killing of the larvae and separation of the biomass of the larvae into a liquid fraction and a pulp fraction, in one single step. Because the temperature to which the living larvae are subjected in advance of being separated into a liquid and a pulp fraction remains sufficiently low, the chitin rich pulp contains a smaller amount of proteins compared to the situation where scalded larvae would be subjected to the same treatment. Moreover, hydrolysis of fats and/or proteins, as well as their degradation by micro-organisms in the course of the grinding step, may be reduced to a minimum. Additionally, due to the presence of the mesh-shaped material, the liquid fraction may be separated from the pulp fraction while moving the biomass through the equipment. The liquid fraction is squeezed through the gauze-shaped material and the pulp fraction is pressed towards the output of the worm screw.

So as to practice the above method, an apparatus can be used for separating the larvae into a pulp and a liquid fraction, such apparatus comprising:
  a) at least two counter-rotating screws for grounding, resp. crushing the larvae;

b) a transport screw placed in a gradually narrowing cylinder whereby the cylinder over the entire length of the transport screw is equipped with a mesh-shaped material.

According to a preferred mode of operation of the method of the invention, the transport screw is a worm screw.

More specifically, the invention relates to a method as set forth in the attached claims.

The method of the invention is suitable for processing larvae of insects.

As indicated above, it is more specifically beneficial to be used for the processing of living larvae, even more particular to the living larvae of one of the following species:
Black Soldier Fly (*Hermetia Illucens*);
Common Housefly (*Musca Domestica*);
Yellow Mealworm (*Tenebrio Molitor*);
Lesser Mealworm (*Alphitobius Diaperinus*);
House cricket (*Acheta Domesticus*);
Banded Cricket *Gryllodes Sigillatus*);
(Jamaican) Field Cricket (*GrYllus Assimilis*).

BRIEF DESCRIPTION OF THE DRAWINGS

With the aim of better illustrating the characteristics of the present invention, as an example without any restrictive nature, some preferred modes of implementation of the method of the present invention are described, with reference to the drawings.

In these drawings, the following is shown.

DESCRIPTION OF THE INVENTION

Figure 1:
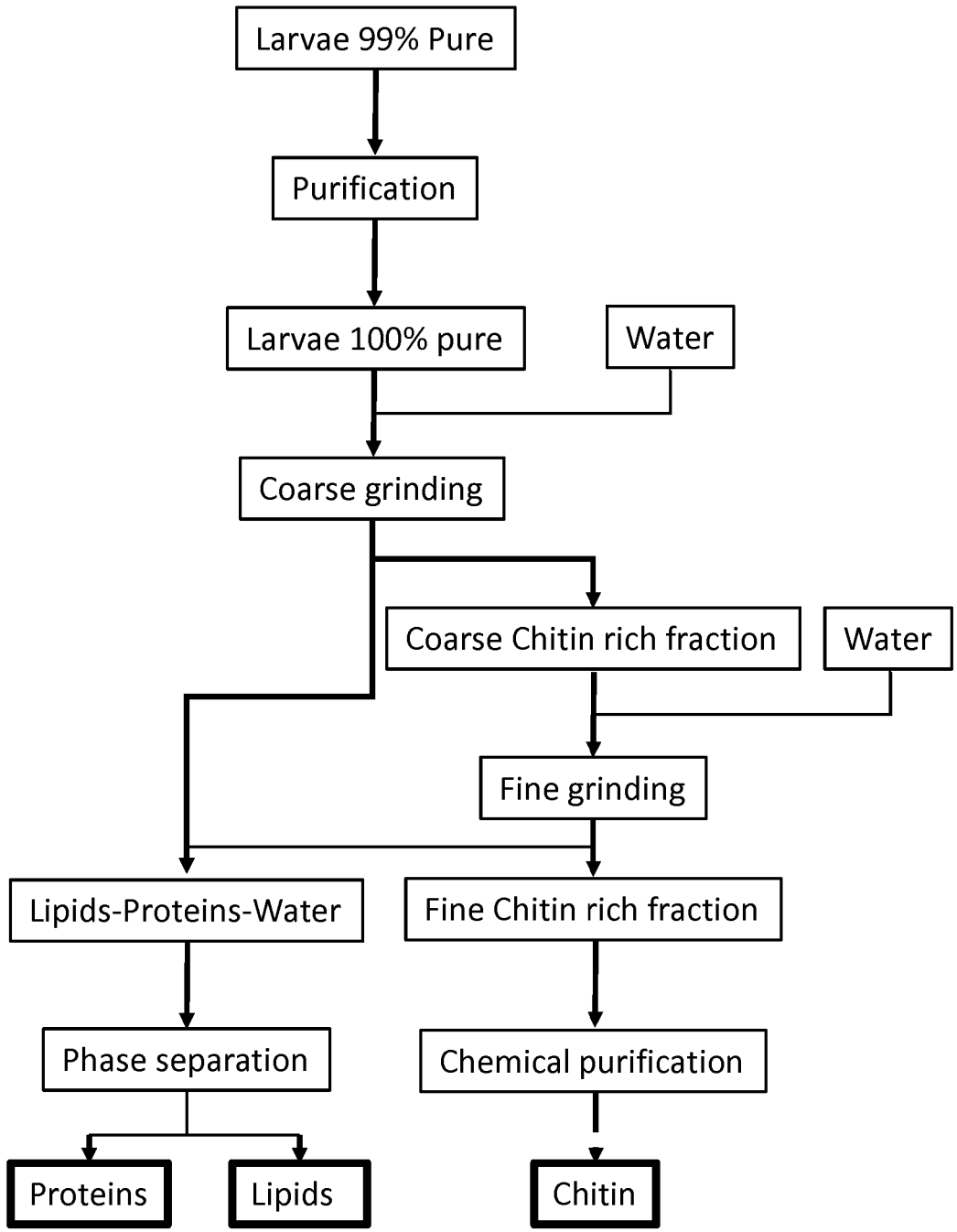
FIG. 1 shows a schematic overview of the steps applied in the method according to the invention, situated within a global approach to the separation of the larvae biomass in proteins, fats and chitin.

The invention relates to a method for the separation of the biomass of larvae in a pulp on the one hand and a liquid fraction on the other hand.

The method thereby comprises the following steps:
a) introducing living larvae into a grinding apparatus whilst adding water;
b) grinding the larvae by means of the grinding apparatus comprising at least two counter-rotating screws to generate ground biomass, and
c) separating the ground biomass into a pulp and a liquid fraction by means of a transport screw placed in a gradually narrowing cylinder, whereby the cylinder at least over the length of the transport screw is equipped with a mesh-shaped material, by squeezing the liquid fraction through the mesh-shaped material and pressing, resp. transporting the pulp fraction towards an outlet of the transport screw.

As mentioned above, the invention can be applied to the larvae of many insects; preferably it is applied to the larvae of the black soldier fly (*Hermetia illucens*) because these larvae are large processors of many types of organic waste streams. Moreover, the biomass of these larvae has a high concentration of fats. The present invention is also suitable or use with, other larvae, including those of the mealworm (*Tenebrio molitor*), etc. . . . .

Results Obtained by Applying the Method According to the Invention

The method according to the invention aims to separate the biomass of the larvae into fractions that can be isolated and further used in economically interesting applications and that way be monetized in the economy.

It is known that insects and/or larvae contain chitin and that such chitin and/or derivatives thereof can be used in multiple cosmetic, medicinal and other (e.g. industrial, see above) applications.

However, obtaining relatively pure chitin from the biomass of insects or insect larvae is a technologically difficult challenge, especially if such separation technique is to be used on larger, production scale and at a minimal cost, which also permits to recover other valuable larval components to the best possible extent.

Known alternative procedures involve burning off protein with expensive and polluting acids or bases; however, this implies an economic loss of protein and is also an expensive process.

When the method according to the invention is applied, the separation of the chitin fraction also yields a residual fraction, rich in fats and proteins.

This group can also be valued economically.

Because, when practicing the method of the invention, both of the above goals can be realized in an economically profitable way, the method of the present invention is suitable for being applied on a large-scale basis.

As such, it makes a substantial contribution to the processing and the valorization of the ever-increasing organic waste quantities in our society.

Prior Purification Step

Prior to the application of the method according to the invention, the biomass of the larvae is preferably purified.

This purification step mainly seeks to remove unwanted impurities, such as hard metal particles which would damage the apparatus used in the method according to the invention. This purification step also aims to remove impurities such as paper or plastic from the biomass; their presence would, after all, be able to block or clog up the device used in the process according to the invention.

The removal of these impurities will also positively influence the quality of the finished products obtained by the application of the method according to the invention, in particular the chitin fraction.

The above-mentioned impurities can be removed from the biomass of the larvae using one of the techniques known to the skilled person, for example by blowing a light air flow over the biomass;

or through a vibrating perforated feed belt or strap; or via magnets that attract metal particles; or by means of an optical sorting technique or manually/visually by an operator; or through a combination of these techniques.

Figure 6:
FIG. 6 shows the larvae, suitable for being subjected the method according to the invention.
Figure 7:
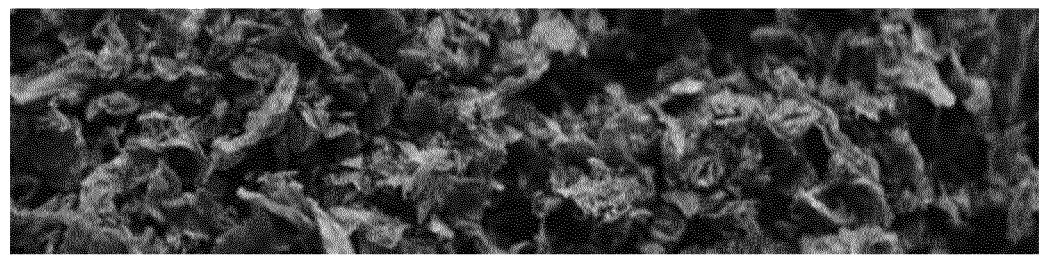
FIG. 7 shows the pulp, resulting from the method according to the invention.

After the application of this purification step, pure larvae, as shown in FIG. 6, are suitable to be separated into the various component groups according to the method according to the invention.

Addition of Water to the Larvae:

The first step in the process or method according to the invention includes the addition of water to the larvae. The addition of water should be carried out simultaneously with feeding the larvae to the grinder, hence the first step of the method reading as 'introducing living larvae into a grinding apparatus whilst adding water'.

The quantity as well as the temperature of the water shall be determined within desired limits to obtain the intended outcome of the method according to the invention.

The addition of water to the living larvae provides unexpected benefits. The processing capacity of the larvae in the method according to the invention is largely dependent on the dry matter content in the biomass of the larvae.

If no water is added, the larvae biomass risks to rapidly turn into a viscous paste or cake that blocks the operation of the device.

Consequently, the processing has to be stopped and the intended separation in the desired constituents may not be attained. The dry matter content in larvae is usually about 40%, expressed as a percentage by weight.

When the larvae are mixed with water in advance of being subjected to grinding, these problems do not occur.

The amount of water to be mixed with the biomass of the larvae is preferably between 50 and 120%, with further preference between 60 and 100% and most preferably between 70 and 80%, all percentages expressed in weight % relative to the weight of the larvae. Higher amounts of water risk to adversely affect the efficiency of the separation process because the process results in too wet of a mush. The temperature of the added water is preferably between and 90° C., with further preference between 40 and 80° C., and most preferably between 50 and 70° C. An appropriate selection of the temperature of the added water assists in improving the efficiency of the method of separation according to the invention.

A substantial benefit of adding hot water to the larvae is as follows: when no water is added, the liquid fraction formed in the course of the pressing step suffers from foaming. As a result, the subsequent step, in particular the separation of the liquid fraction into fats and proteins, should take place within a very limited time frame.

The inventors have found that the addition of water in an amount as described above, and with the temperature as described above, counteracts foam formation. The subsequent separation step in fats and proteins become less cumbersome and can be realized much easier.

Figure 2:
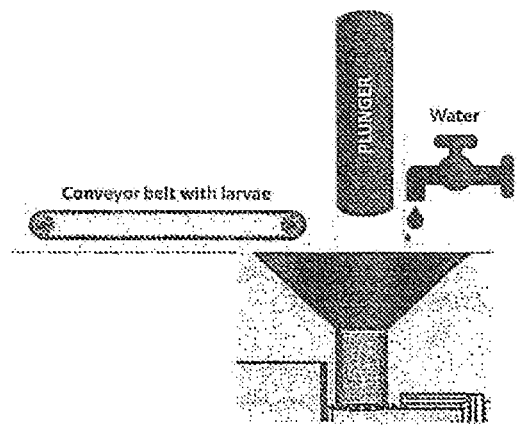
FIG. 2 schematically shows the apparatus for mixing the larvae with water, and feeding same in a funnel for input into the counter-rotating screws in accordance with the method according to the invention.

In FIG. 2, a basic arrangement shows how the larvae and the water are added to the device in the method according to the invention.

The preferably "pre-purified" larvae are, in a preferred embodiment of the invention, supplied into a funnel via a continuous supply belt or band. To this funnel also water is supplied.

Preferably, the water/larvae mixture is conveyed under pressure from the funnel towards the counter-rotating screws of the grinding device.

Application of pressure significantly increases the throughput capacity of the installation and purity of the pulp. This can be achieved by using a cylindrical channel, placed at the bottom of the funnel and the counter-rotating screws.

At the top, preferably, a stamper or plunger is installed which pressures the mixture into the crushing or grounding device.

According to the present invention, the larvae are fed as living larvae into the funnel, whilst water is being added.

The researchers have found that, for example, when using frozen larvae, the separation step following the method of the invention is significantly less efficient. In such a case, the separation between the chitin and the protein fraction is substantially less efficient. The pulp fraction e.g. contains more proteins and fat.

Similarly, when dead larvae are fed to the grounding apparatus, e.g. by adding hot, boiling water to the larvae before introduction into the funnel or the grinding apparatus, as described in the abovementioned WO 2016/108033 A1, the majority of the protein fraction of the larvae will end up into the pulp, chitin-rich fraction. From this fraction, the protein can only be extracted by an additional hydrolysis step, a.o. as described WO 2016/108033.

Contrary thereto, when applying the method according to the present invention, the larger part of the protein contained in the larvae will be separated into the liquid fraction, together with the fat fraction of the larvae. Thereupon, the protein can be separated from the fat fraction in a decanter. This is a quite unexpected advantage resulting from the application of the present invention; this advantage is quite unexpected and not suggested by WO 2016/108033.

Grinding Step

A next step in the process according to the invention is to grind the larvae by means of counter-rotating screws.

Figure 5:
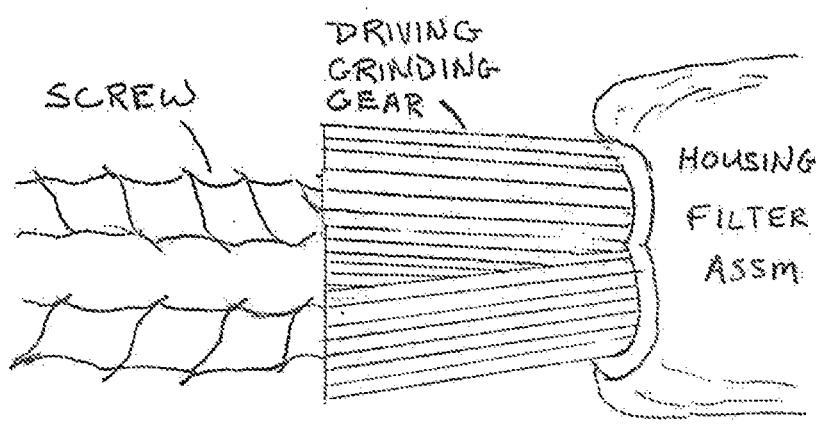
FIG. 5 shows a detail of the counter-rotating screws of the apparatus used in the method according to the invention.

FIG. 5, right part, shows an example of such counter-rotating screws or worm wheels.

The counter-rotating screws include, for example, two spiral screws, which rotate in opposite directions, and at the ends of which the respective propeller blades overlap.

Parts of the grinding system are set up in a custom-made housing. The casing closely follows the profile of the screws, i.e. the spacing between the casing and the screws is quite limited.

Because the screws are operated, made to rotate in opposite direction, the larvae are crushed, ground and forwarded towards the output/outlet of both screws. Preferably, the screws and the housing in which they are positioned are made of stainless steel.

Preferably, the rotational speed of the screws is limited, and is comprised between 50 and 150 rpm, more preferably between 75 and 125 rotations per minute.

The screws are preferably driven by an electrical motor.

An example of an apparatus that can be used in the method according to the invention is the juice producing device marketed under the name "Angel Juicer", type 20 k, 60 K or 140K, for example, available via the website 'slowjuice.nl' or 'ahealthylife.nl'.

The pressure force necessary for the grinding of the larvae is automatically set by the device.

The Angel 20-K can handle about 20 kilogram per hour, the Angel 60-K can handle up to 60 kilogram per hour.

This Juicer runs at 82 rpm; this speed is suitable for grinding the larvae of the black soldier fly. Preferably, a speed is maintained in the range from 60 to 100 rpm, more preferably from 70 to 90 rpm, most preferably about 80 rounds per minute.

Figure 4:
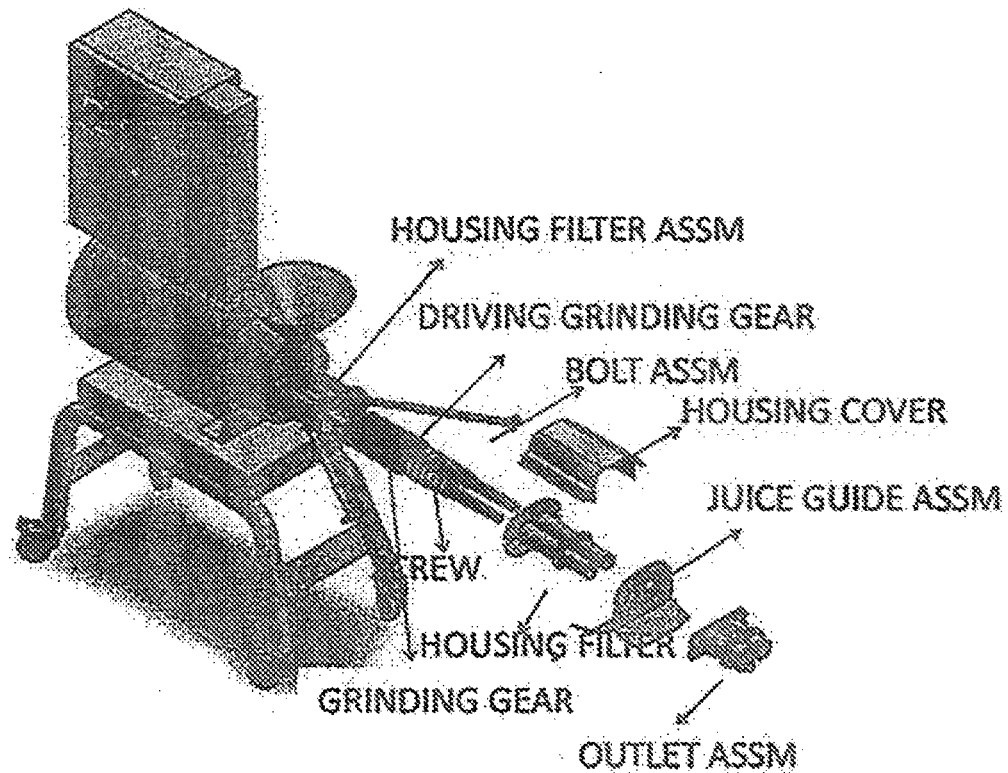
FIG. 4 also shows a specific implementation of the apparatus used in the method according to the invention, now in a partially disassembled view.

FIG. 4 shows an image in perspective of such Angel 60-K Juicer, which can be used for the application in the method according to the invention.

Separation Steps:

After the mixture of larvae and water has been ground by the counter-rotating screws, the ground mixture is separated into two fractions:
- a pulp fraction, this is the chitin-rich fraction, and
- a liquid fraction, rich in fats and proteins.

According to a preferred setup of the invention, the pulp and the liquid fraction are separated from the chitin rich fraction by applying an increasing pressure on the milled larvae.

According to a further preferred setup of the invention, such pressure is realized when the ground larvae are pressed by means of a worm screw through a narrowing housing in the form of a cylindrical casing.

The casing follows the profile of the transport, preferably the worm screw (limited spacing between both of these parts), and is equipped with a mesh-shaped material.

The separation takes place as the liquid fraction passes through this mesh-shaped material of the narrowing cylindrical casing and the pulp is squeezed at the end of the narrowing cylindrical casing.

The pressure in the apparatus, more particularly in the portion of the transport, resp. worm screw (or transport, resp. worm screws) and the passing gauze-shaped material, can be adapted, by adapting the dimensions of the outlet. Thereto adequate means are provided, which are generally known to the skilled person. In a preferred embodiment use is made of an adjustment bolt, an adjusting screw, a levelling screw of equivalent means, placed at the end of the transport, resp. worm screw or transport, resp. worm screws and the passing mesh-shaped material.

Such adjustment means, e.g. the adjustment bolt determines the free space through which the pulp is pushed out. The smaller this space is set, the higher the pressure in the unit is built up.

As indicated above, the liquid fraction contains mainly the fats and proteins, while the chitin of the larvae is present mainly in the pulp fraction.

Figure 3:
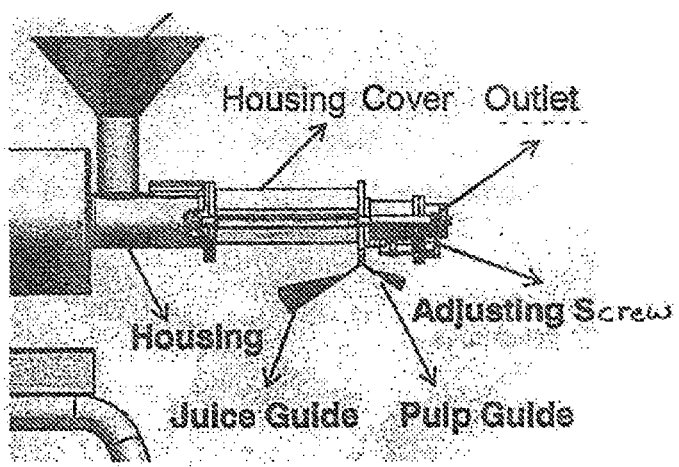
FIG. 3 shows a schematic overview of the apparatus used in the method according to the invention.

As indicated in FIG. 3, at the end of the screws in the cylindrical housing, two fittings are placed at the bottom of the housing (a juice conductor and a pulp conductor) through which the liquid fraction and the pulp group, respectively, are led for reception in the intended collection trays.

After the method according to the invention has been applied to the larvae to be ground and separated, a rough-grind chitin-rich pulp fraction is obtained.

This is an irregularly shaped material, which usually still contains a substantial amount of fats and proteins.

The presence of fats and proteins in this chitin-rich pulp can be further reduced by retreating this pulp fraction according to the method of this invention.

In other words, this chitin-rich pulp is then re-mixed with warm water, re-inserted into the funnel and in the grinding section of the device, put under pressure by a stamper or plunger, then again split into a chitin-rich pulp fraction and a lipid-and-protein-rich liquid phase.

After the second application of this method according to the invention, a uniform chitin-rich pulp is obtainable, in which the proportion of fats and proteins is significantly reduced compared to the pulp after the first passage through the device.

Figure 8:
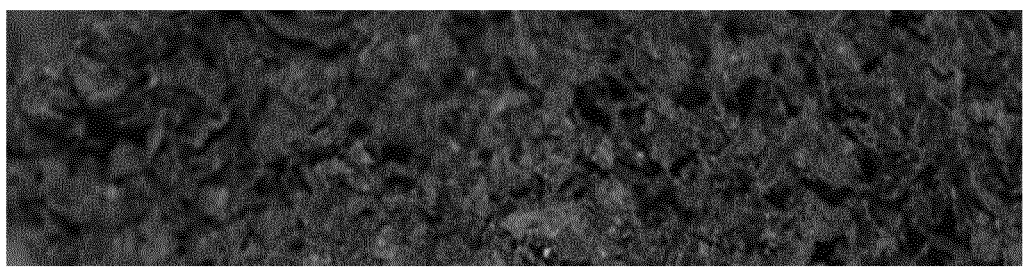
FIG. 8 shows the pulp, resulting from the method according to the invention, when the method of the invention has been applied a second time, especially on the pulp resulting from a first application of the method according to the invention.

This refined pulp fraction is shown in FIG. 8.

In a test or experiment as described below, this second passage through the device produced 10% more fat/protein mixture, and a corresponding reduction of impurities in the fine chitin pulp fraction.

Practical Example of Operation of the Method According to the Invention (Preferred Mode).

In order to further illustrate a preferred mode of operation of the method according to the invention, the following test was run:

158 kg of larvae were mixed with 158 kg of water and continuously dosed on the funnel as shown in FIGS. 2 and 3. In total, a biomass of 316 kg, with a dry matter content of 54 kg, is therefore processed.

On this biomass the method according to the invention is applied and this yielded 51 kg of raw chitin-rich pulp, with a dry matter content of 20 kg.

To the obtained 51 kg of raw pulp then 50 kg of water was added, and this mixture was processed again by the method according to the invention.

This resulted in the following component groups:
- 23 kg fine chitin-rich pulp, with a dry matter content of 13 kg.
- a liquid fraction, rich in fats and proteins, added to the original liquid fraction originating from the first application of the method according to the invention.

Further Processing Steps:

As indicated above, the liquid fraction obtained by the method according to the invention should preferably be treated immediately. Ideally it is kept in a closed tank, before being pumped to a subsequent device for further processing.

The addition of the hot water ensures that the liquid fraction is somewhat stabilized. Without this addition, this fraction would immediately start foaming and quasi-immediately become viscous and sticky.

The fine chitin-rich fraction can be stored in a chilled room for several days, where it can be dried.

The invention claimed is:

1. A method for separating the biomass of larvae into a pulp and a liquid fraction, comprising the following steps:
   a) introducing living larvae into a grinding apparatus whilst adding water;
   b) grinding the larvae by means of the grinding apparatus comprising at least wo counter-rotating screws to generate ground biomass; and
   c) separating the ground biomass into a pulp and a liquid fraction by means of a transport screw placed in a gradually narrowing cylinder, whereby the cylinder at least over the length of the transport screw is equipped with a mesh-shaped material, by squeezing the liquid fraction through the mesh-shaped material and pressing, and transporting the pulp fraction towards an outlet of the transport screw.

2. The method according to claim 1, characterized in that the quantity of water added to the larvae is comprised between 50 and 120%, all percentages expressed in weight % of water versus weight of larvae.

3. The method according to claim 1, characterized in that the temperature of the added water is comprised between 30 and 90° C.

4. The method according to claim 1, characterized in that the grinding of the larvae includes bruising, crushing, milling and/or pressing acts exerted on the larvae; and in that the larvae are fed to the counter-rotating screws under pressure.

5. The method according to claim 1, characterized in that the pulp and the liquid fraction are separated under the influence of pressure on the ground larvae.

6. Method according to claim 4, characterized in that the pressure on the ground larvae increases as the ground biomass is pressed by the transport screw through the narrowing cylinder.

7. Method according to claim 1, characterized in that the larvae are fed into the grinding apparatus via a funnel.

8. Method according to claim 1, applied to larvae of the black soldier fly.

9. Method according to claim 1, wherein the pulp is recovered.

10. Method according to claim 1, characterized in that the resulting pulp fraction is chitin-rich and the resulting liquid fraction is fat-and protein-rich.

11. Method according to claim 1, wherein the transport screw is a worm screw.

12. The method according to claim 1, characterized in that the quantity of water added to the larvae is comprised between 60 and 100%, all percentages expressed in weight % of water versus weight of larvae.

13. The method according to claim 1, characterized in that the quantity of water added to the larvae is comprised between 70 and 80%, all percentages expressed in weight % of water versus weight of larvae.

14. The method according to claim 1, characterized in that the temperature of the added water is comprised between 40 and 80° C.

15. The method according to claim 1, characterized in that the temperature of the added water is comprised between 50 and 70° C.

\* \* \* \* \*